United States Patent
Geilen et al.

(10) Patent No.: US 11,773,041 B2
(45) Date of Patent: *Oct. 3, 2023

(54) PROCESS FOR PREPARING ALDEHYDES AND COOLING A STREAM OF MATTER

(71) Applicant: Evonik Operations GmbH, Essen (DE)

(72) Inventors: Frank Geilen, Haltern am See (DE); Alexander Brächer, Haltern am See (DE); Stefan Drees, Duelmen (DE); Benedikt Dereks, Bochum (DE); Robert Franke, Marl (DE); Ana Markovic, Haltern am See (DE); Armin Matthias Rix, Marl (DE); Martin Oldemeyer, Haltern am See (DE); Dirk Fridag, Haltern am See (DE)

(73) Assignee: Evonik Operations GmbH, Essen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/055,989

(22) Filed: Nov. 16, 2022

(65) Prior Publication Data
US 2023/0159425 A1    May 25, 2023

(30) Foreign Application Priority Data
Nov. 19, 2021  (EP) .................................... 21209276

(51) Int. Cl.
*C07C 45/50*    (2006.01)

(52) U.S. Cl.
CPC ........ *C07C 45/505* (2013.01); *C07C 2523/46* (2013.01)

(58) Field of Classification Search
CPC ......... C07C 45/50; C07C 45/62; B01J 23/464
See application file for complete search history.

(56) References Cited

U.S. PATENT DOCUMENTS

| 2008/0251456 A1 | 10/2008 | Wiese et al. |
| 2012/0046503 A1 | 2/2012 | Priske et al. |
| 2016/0002136 A1 | 1/2016 | Lueken et al. |

FOREIGN PATENT DOCUMENTS

| WO | 2007/036424 | 4/2007 |
| WO | 2010/097376 | 9/2010 |
| WO | 2014/131623 | 9/2014 |

OTHER PUBLICATIONS

U.S. Appl. No. 18/055,442, filed Nov. 15, 2022, Markovic et al.
European Search Report dated Mar. 28, 2023, in European Applicatiion No. 22205989.1, 8 pages.
U.S. Office Action dated Mar. 14, 2023, in U.S. Application No. 18/055,442, 6 pages.

*Primary Examiner* — Sikarl A Witherspoon
(74) *Attorney, Agent, or Firm* — Grüneberg and Myers PLLC

(57) ABSTRACT

A process for preparing aldehydes by a homogeneously catalyzed hydroformylation of $C_4$ to $C_{20}$ olefins involves withdrawing a biphasic stream (liquid/gaseous) and expanding in two stages. Before, between, or after the two stages, the liquid phase is cooled. Only after expansion and cooling is the homogeneously dissolved rhodium catalyst system separated from the residual stream in a three-stage removal.

20 Claims, No Drawings

PROCESS FOR PREPARING ALDEHYDES AND COOLING A STREAM OF MATTER

CROSS-REFERENCE TO RELATED APPLICATIONS

This application claims priority to European Application No. 21209276.1, flied on Nov. 19, 2021, the content of which is hereby incorporated by reference in its entirety.

BACKGROUND OF THE INVENTION

Field of the Invention

The present invention relates to a process for preparing aklehydes by a homogeneously catalyzed hydroformylation of $C_4$ to $C_{20}$ olefins, in which a biphasic stream (liquid/gaseous) is withdrawn and expanded in two stages. Before those, between those or after those, the liquid phase is cooled. Only after expansion and cooling is the homogeneously dissolved rhodium catalyst system separated from the residual stream in a three-stage removal step.

Description of Related Art

The separation of homogeneously dissolved rhodium catalyst systems from the hydroformylation mixtures obtained is a demanding technical problem which is solved in the chemical industry, for example, by an evaporation of the crude product stream and/or an organophilic nanofiltration. What is common to the two separation processes is that they are generally conducted at distinctly lower pressures than the preceding hydroformylation reaction itself. Since the hydroformylation is typically conducted with a significant excess of synthesis gas, at least a portion of the synthesis gas will dissolve in the reaction mixture. Therefore, upstream of the separation processes may be disposed, for example, an expansion of the reactor output obtained from the hydroformylation, in order to remove dissolved synthesis gas (see WO 2014/131623 A1 and the overview of the known prior art therein).

Proceeding from the known prior art, a constant problem is that of optimizing the hydroformylation and the downstream process steps. A main focus of attention here is on the separation of the rhodium catalyst system from the reaction mixtures because rhodium is a very costly precious metal and losses should be avoided if at all possible. Such catalyst losses may occur at various points in the process, for example in the membrane separation according to the already cited WO 2014/131623 A1. The fact that certain amounts of catalysts can also be lost at other points in the process has to date played only a minor role in the prior art.

The problem addressed by the present invention was therefore that of providing a process for the hydroformylation of olefins, in which a suitable workup of the reaction mixtures obtained results in lower losses of the rhodium catalyst system than in processes known from the prior art.

This problem was solved by the process described in accordance with the invention for preparing aldehydes by hydroformylation of olefins as described below. Preferred configurations are also specified below.

The process according to the invention is accordingly a process for preparing aldehydes by hydroformylation of olefins, wherein the process comprises the following steps:

a) hydroformylating $C_4$ to $C_{20}$ olefins, preferably $C_6$ to $C_{12}$ olefins, in a reaction zone in the presence of synthesis gas and a homogeneous rhodium catalyst system at a pressure of 100 to 350 bar and a temperature of 90° C. to 250° C., preferably 110° C. to 250° C., to obtain a biphasic hydroformylation mixture, i.e. one comprising a gas phase and a liquid phase, containing at least unconverted olefins, synthesis gas, the homogeneous rhodium catalyst system and the aldehydes formed, which is withdrawn from the at least one reaction zone;

b) firstly expanding the hydroformylation mixture to a pressure between 11 bar and 50 bar, and separating the hydroformylation mixture into a first gaseous phase especially comprising the synthesis gas, and a first liquid phase especially comprising the unconverted olefins, the homogeneous rhodium catalyst system and the aldehydes formed;

c) secondly expanding the first liquid phase obtained from step b) to a pressure between 1 bar and 10 bar, and separating it into a second gaseous phase especially comprising the synthesis gas, and a second liquid phase especially comprising the unconverted olefins, the homogeneous rhodium catalyst system and the aldehydes formed; and d) feeding the second liquid phase to an at least three-stage removal, wherein. In the first stage, a first membrane separation is effected, in which the rhodium catalyst system is enriched in the retentate and the permeate is directed to the next stage;

in the second stage, the permeate from the first membrane separation is subjected to a thermal separation in which at least a portion of the aldehydes formed is removed together with the top product, and the liquid bottom product is directed to the next stage; and in the third stage, the liquid bottom product from the thermal separation is subjected to a second membrane separation in which the rhodium catalyst system is enriched in the retentate, characterized in that the biphasic hydroformylation mixture prior to the first expansion in step b), the first liquid phase prior to the second expansion in step c), or the second liquid phase prior to the feeding to a removal in step d) is cooled to a temperature between 40 and 100° C.

The invention also includes the following embodiments:

1. Process for preparing aldehydes by hydroformylation of olefins, wherein the process comprises the following steps:

a) hydroformylating $C_4$ to $C_{20}$ olefins, preferably $C_6$ to $C_{12}$ olefins, in a reaction zone in the presence of synthesis gas and a homogeneous rhodium catalyst system at a pressure of 100 to 350 bar and a temperature of 90° C. to 250° C. to obtain a biphasic hydroformylation mixture, i.e. one comprising a gas phase and a liquid phase, containing at least unconverted olefins, synthesis gas, the homogeneous rhodium catalyst system and the aldehydes formed, which is withdrawn from the at least one reaction zone;

b) firstly expanding the hydroformylation mixture to a pressure between 11 bar and 50 bar, and separating the hydroformylation mixture into a first gaseous phase especially comprising the synthesis gas, and a first liquid phase especially comprising the unconverted olefins, the homogeneous rhodium catalyst system and the aldehydes formed;

c) secondly expanding the first liquid phase obtained from step b) to a pressure between 1 bar and 10 bar, and separating it into a second gaseous phase especially comprising the synthesis gas, and a second liquid phase especially comprising the unconverted olefins, the homogeneous rhodium catalyst system and the aldehydes formed; and d) feeding the second liquid phase to an at least three-stage removal, wherein, in the first stage, a first membrane separation is effected, in which the rhodium catalyst system is enriched in the retentate and the permeate is directed to the next stage;

in the second stage, the permeate from the first membrane separation is subjected to a thermal separation in which at least a portion of the aldehydes formed is removed together with the top product, and the liquid bottom product is directed to the next stage; and in the third stage, the liquid bottom product from the thermal separation is subjected to a second membrane separation in which the rhodium catalyst system is enriched in the retentate, characterized in that the biphasic hydroformylation mixture prior to the first expansion in step b), the first liquid phase prior to the second expansion in step c), or the second liquid phase prior to the feeding to a removal in step d) is cooled to a temperature between 40 and 100° C.

2. Process according to embodiment 1, wherein the cooling is conducted in two steps, of which the first cooling takes place after the hydroformylation in step a) and before the first expansion in step b) and the second cooling takes place after the second expansion in step c) and before the removal in step d).

3. Process according to embodiment 1 or 2, wherein the hydroformylation in step a) is effected at a pressure between 175 and 300 bar, preferably 200 to 280 bar.

4. Process according to any of the preceding embodiments, wherein the hydroformylation in step a) is effected at a temperature in the range from 120 to 200° C., preferably 120 to 180° C.

5. Process according to any of the preceding embodiments, wherein the olefin used in the hydroformylation also functions as solvent.

6. Process according to any of the preceding embodiments, wherein the catalyst system used in the hydroformylation comprises not only rhodium but also a phosphorus-containing ligand.

7. Process according to any of the preceding embodiments, wherein the expansion in step b) and/or in step c) is into a vessel in which gas phase and liquid phase can be separated.

8. Process according to any of the preceding embodiments, wherein the cooling is effected by means of a discharge cooler.

9. Process according to any of the preceding embodiments, wherein the membrane separations in step d) are effected at a temperature between 20 and 80° C., preferably 40 to 70° C.

10. Process according to any of the preceding embodiments, wherein the transmembrane pressure in the membrane separations in step d) is between 15 and 50 bar, preferably between 20 and 45 bar.

11. Process according to any of the preceding embodiments, wherein the rhodium catalyst system is obtained in the retentate in the membrane separations in step d) and the retentate from the first membrane separation is returned to the reaction zone in step a) and the retentate from the second membrane separation is recycled upstream of the first membrane separation in step d).

12. Process according to any of the preceding embodiments, wherein the thermal separation is a distillation, a thin-film evaporation, a falling-film evaporation or a combination of two or more of these.

13. Process according to embodiment 12, wherein the thermal separation is a thin-film evaporation, a falling-film evaporation or a combination of thin-film evaporation and falling-film evaporation.

14. Process according to embodiment 11 or 13, wherein the thermal separation is multistage falling-film evaporation.

15. Process according to any of the preceding embodiments, wherein the aldehydes obtained from the process are sent to a downstream process step, for example a hydrogenation or an oxidation.

DETAILED DESCRIPTION OF THE INVENTION

The process according to the invention has the advantage that the cooling prior to the expansion can demonstrably reduce rhodium loss. The process according to the present invention accordingly offers significant economic benefits since rhodium is very costly. It also has environmental benefits because less rhodium precipitates out and has to be removed and disposed of in a costly and inconvenient manner. Furthermore, the process is advantageous owing to the two-stage expansion. The two-stage expansion prevents additional precipitation of rhodium as a result of an excessive and excessively rapid reduction in pressure. Furthermore, the two-stage expansion prevents foaming in the reaction solution to be expanded. Foaming leads to problems in the downstream process steps.

In the first step a), the $C_4$ to $C_{20}$ olefins, preferably $C_8$ to $C_{12}$ olefins, used are first hydroformylated. The hydroformylation takes place here as usual in the presence of synthesis gas (a mixture of CO and $H_2$) and a homogeneously dissolved rhodium catalyst system.

Suitable hydrocarbon streams are typically used for the provision of the olefins in the process according to the invention. The $C_4$ to $C_{20}$ olefins, preferably $C_8$ to $C_{12}$ olefins, envisaged in accordance with the invention for the hydroformylation may be olefins having terminal and/or internal C—C double bonds. The hydrocarbon streams mentioned may also comprise olefins having the same number or different numbers of carbon atoms. Suitable olefins are especially 1- or 2-butene or mixtures thereof, isobutene, 1- or 2-pentene or mixtures thereof, isopentenes, 1-, 2- or 3-hexene, 1-heptene, linear heptenes with an internal double bond (2-heptene, 3-heptene, etc.), mixtures of linear heptenes, 2- or 3-methyl-1-hexene, 1-octene, linear octenes with an internal double bond, mixtures of linear octenes, 2-, 3- or 5-methylheptenes, 2-ethylhexenes, 2-ethyl-3-methylpentenes, 3,4-dimethylhexenes, or mixtures of the aforementioned linear and branched $C_8$ olefins (called di-n-butene), 2,4,4-trimethylpentenes (called diisobutene), mixtures of di-n-butene and diisobutene, 1-nonene, linear nonenes with an internal double bond, mixtures of linear nonenes, 2-, 3- or 4-methyloctenes, 1-, 2-, 3-, 4- or 5-decene, 2-ethyl-1-octene, 1-dodecene, linear dodecenes with an internal double bond, branched dodecenes (meaning branched olefins having 12 carbon atoms) with a terminal or internal double bond, mixtures of such linear and branched dodecenes (called tri-n-butene), 1-tetradecene, linear tetradecenes with an internal double bond, mixtures of linear tetradecenes, 1-hexadecene, linear hexadecenes with an internal double bond and mixtures of linear hexadecenes.

C$_5$ olefins, i.e. pentenes, are present in light petroleum fractions from refineries or crackers. Industrial mixtures comprising C$_4$ olefins, i.e. n-butene and isobutene, are light petroleum fractions from refineries, C$_4$ fractions from FC crackers or steam crackers, mixtures from Fischer-Tropsch syntheses, mixtures from dehydrogenation of butanes, and mixtures resulting from metathesis or other industrial processes. The higher olefins can in particular be obtained by oligomerization reactions, for example dimerization, trimerization or tetramerization. Suitable hydrocarbon streams are in addition the mixture of isomeric hexenes (dipropene) resulting from the dimerization of propene, the mixture or isomeric octenes (dibutene) resulting from the dimerization of butenes, the mixture of isomeric nonenes (tripropene) resulting from the trimerization of propene, the mixture of isomeric dodecenes (tetrapropene or tributene) resulting from the tetramerization of propene or the trimerization of butenes, the isomeric hexadecene (tetrabutene) resulting from the tetramerization of butenes and also the olefin mixtures produced by the co-oligomerization of olefins having a varying number of carbon atoms (preferably 2 to 4 carbon atoms), optionally after distillative separation into fractions having the same or different numbers of carbon atoms. Olefins or olefin mixtures produced by Fischer-Tropsch synthesis may also be used. It is additionally possible to use olefins produced by olefin metathesis or by other industrial processes.

The olefins used in the process are hydroformylated with synthesis gas. The synthesis gas. i.e. a mixture of carbon monoxide and hydrogen, for the process according to the invention may be used in different mixing ratios of carbon monoxide and hydrogen. The molar ratio between synthesis gas and the hydrocarbon stream used that contains the olefins to be hydroformylated should be between 6:1 and 1:1, preferably between 3:1 and 1:1, more preferably between 2:1 and 1:1. The hydroformylation can optionally be conducted in the presence of an additional solvent known to the person skilled in the art, but preference is given to adding no additional solvent, with the olefin used instead functioning as solvent in the hydroformylation.

The homogeneous rhodium catalyst system used in the hydroformylation in step a) of the process according to the invention comprises or consists of rhodium (Rh) and preferably a phosphorus-containing ligand. Suitable ligands for the catalyst systems of the invention are known to those skilled in the art (see e.g. the textbooks "Rhodium Catalyzed Hydroformylation" (from 2002) by P. W. N. M. van Leeuwen or "Hydroformylation—Fundamentals, Processes and Applications in Organic Synthesis" (from 2016) by A. Börner and R. Franke). The phosphorus-containing ligand for the catalyst system of the invention is preferably a phosphine (e.g. TPP (triphenylphosphine)), a monophosphite (e.g. Alkanox 240 (tris(2,4-di-tert-butylphenyl)phosphite)) or a bisphosphite (e.g. BiPhePhos). It is also possible to use mixtures of ligands. The rhodium concentration in the reaction zone in step a) Is preferably between 10 and 80 ppm, more preferably between 30 and 50 ppm.

In a preferred embodiment of the present invention, the rhodium catalyst system, prior to entry into the reaction zone, is dissolved in at least a portion of the solvent, i.e., for example, the olefins used or the hydrocarbon stream used that contains the olefins used, and then fed to the reaction zone. This has the advantage that the catalyst system already arrives in dissolved form in the reaction zone and need not be dissolved therein before it can catalyze the hydroformylation. The resulting solution of rhodium catalyst system in olefin/solvent may be preheated prior to entry into the reaction zone. As a result, there is no need to use any energy for the heating in the reaction zone.

The hydroformylation in step a) of the process according to the invention is conducted under the following conditions: The temperature in the hydroformylation is within a range from 90° C. to 250° C., preferably 110° C. to 250° C., more preferably within a range from 120 to 200° C. and particularly preferably within a range from 120 to 160° C. The pressure in the hydroformylation is within a range from 100 to 350 bar, preferably within a range from 175 to 300 bar and more preferably within a range from 200 to 280 bar.

The hydroformylation is according to the invention carried out in at least one reaction zone. A reaction zone for the purposes of the present invention comprises at least one reactor in which the hydroformylation is carried out. It is also possible for the reaction zone to comprise more than one reactor, in particular two or three reactors, which can be connected in parallel or in series or arranged in a hybrid of parallel and serial connection.

In the hydroformylation in step a), according to the invention, a biphasic hydroformylation mixture, i.e. one comprising a gas phase and a liquid phase, which contains at least unconverted olefins, synthesis gas, the homogeneous rhodium catalyst system and the aldehydes formed, is obtained. In this case, the synthesis gas is both in dissolved form, i.e. dissolved in the liquid organic phase, and in the form of free synthesis gas, i.e. the gas phase of the biphasic hydroformylation mixture is formed. The hydroformylation mixture may additionally contain high-boiling compounds that can form as by-products in the hydroformylation.

In step b), the optionally cooled hydroformylation mixture obtained is expanded from the present reaction pressure to a pressure between 11 bar and 50 bar, preferably in a suitable vessel in which gas phase and liquid phase can be separated. One example of this is an expansion vessel known from the prior art. This first expansion is preferably conducted in a single step, but may also be effected in multiple component steps. It may also be advantageous when, for each of the component expansion steps, there is at least one vessel for separation of the first liquid phase from the gaseous phase.

The first expansion converts dissolved synthesis gas to the gas phase. Step b) therefore also includes the separation of the hydroformylation mixture into a first gaseous phase comprising synthesis gas to a predominant degree, i.e. to an extent of more than 90% by volume, and a first liquid phase comprising the unconverted olefins, the homogeneous rhodium catalyst system and the aldehydes formed. It is also possible for still-dissolved synthesis gas to be present in the first liquid phase. If high-boiling compounds are additionally also present in the hydroformylation mixture, these high-boiling compounds are likewise present in the first liquid phase.

The first gaseous phase separated off in the separation in step b), especially comprising the synthesis gas, may at least partly be returned to the reaction zone. Recycling is not always desired or required. It may therefore be advantageous when the first gaseous phase separated off is sent to another use, for example production or hydrogen. If the first gaseous phase is returned to the reaction zone, it is preferable that the first gaseous phase is compressed before entry into the reactor(s) of the reaction zone. It is particularly preferable here when the first gaseous phase passes through a cooler beforehand in order to separate off organic vapours and entrained droplets as condensate. The condensate thus obtained may be guided to the liquid phase from the phase separation vessel. It may also be advantageous to free the synthesis gas of impurities, for example of formic acid formed as a by-product in the hydroformylation, by a scrubbing operation prior to further use (recycling or other use). Useful scrubbing media, as well as water and amine-containing aqueous solutions, also include organic solvents. In practice, it has been found to be advantageous to use the high boilers obtained as by-products in the hydroformylation as scrubbing liquid.

The first liquid phase obtained from the separation in step b) is directed into step c) for the second expansion. In this step c), the first liquid phase obtained is expanded from the present pressure from the first expansion to a pressure between 1 bar and 10 bar, preferably in a suitable expansion vessel. In principle, the pressure attained here should be guided by the permeate pressure of the first membrane separation in step d); in particular, the pressure should be somewhat lower than this permeate pressure. This second expansion is preferably conducted in a single step, but may also be effected in multiple component steps. It may also be advantageous when, for each of the component expansion steps, there is at least one expansion vessel for separation of the liquid phase from the gaseous phase.

The second expansion can also convert still-dissolved synthesis gas to the gas phase. The second expansion in step c) therefore also includes the separation of the hydroformylation mixture into a second gaseous phase comprising synthesis gas to a predominant degree, i.e. to an extent of more than 90% by volume, and a second liquid phase comprising the unconverted olefins, the homogeneous rhodium catalyst system and the aldehydes formed. Small amounts of dissolved synthesis gas may additionally be present in the second liquid phase. If high-boiling compounds are additionally also present in the hydroformylation mixture, these high-boiling compounds are likewise present in the first liquid phase.

The second gaseous phase separated off in the separation in step c), especially comprising the synthesis gas, may at least partly be returned to the reaction zone. Recycling is not always desired or required. It may therefore be advantageous when the second gaseous phase separated off is sent to another use, for example production of hydrogen or incineration. If the second gaseous phase is returned to the reaction zone, it is preferable that the second gaseous phase is compressed before entry into the reactor(s) of the reaction zone. It is particularly preferable here when the second gaseous phase passes through a cooler beforehand in order to separate off organic vapours and entrained droplets as condensate. The condensate thus obtained may be guided to the first and/or second liquid phase from the phase separation vessel.

The second liquid phase obtained from the second expansion in step c) is then guided to an at least three-stage removal in step d).

The characterizing feature of the present invention is the cooling of the stream at a point in the process, but no later than before the removal in step d). The cooing of the stream ensures a reduction in the rhodium use factor. The problem is that a small portion of the rhodium is always lost in various ways during a hydroformylation and the subsequent removal. On account of the high costs of rhodium or rhodium compounds, this increases the process costs, because the losses of rhodium have to be compensated for by replenishment. However, the cooling according to the invention has the effect that the use factor falls, i.e. less rhodium is lost and less rhodium also has to be replenished. The process costs can thus be lowered considerably in this way.

In the present context, it is less critical when the cooling is effected, provided that the cooling follows the hydroformylation in step a) and precedes the removal in step d). For instance, the cooing of the biphasic hydroformylation mixture can be conducted before the first expansion in step b), on the first liquid phase before the second expansion in step c), or on the second liquid phase before the feeding to the removal in step d). In a preferred embodiment of the present invention, the cooling takes place on the biphasic hydroformylation mixture, i.e. after the hydroformylation in step a) and before the first expansion in step b). In the cooing, the respective liquid phase to be cooled or the hydroformylation mixture is cooled to a temperature between 40 and 100° C., preferably between 50 and 95° C., more preferably between 60 and 90° C. For this purpose, a suitable cooling apparatus is required, especially for biphasic substance mixtures, when the biphasic hydroformylation mixture is to be cooled. The cooing is especially effected with a discharge cooler. Shell and tube heat exchangers, for example, have been found to be useful, wherein the reaction mixture is preferably guided through the tubes and the cooling medium preferably through the shell of the heat exchanger.

In a further-preferred embodiment of the present invention, the cooling is conducted in two steps. A first cooling operation takes place here on the biphasic hydroformylation mixture, i.e. after the hydroformylation in step a) and before the first expansion in step b), and a second cooling operation on the second liquid phase, i.e. after the second expansion in step c) and before the removal in step d). In the first cooling operation, the mixture present is preferably cooled to a temperature between 80 and 90° C. The second cooling operation preferably involves cooling to a temperature between 35 and 55° C. Preference is given here to the use of a discharge cooler for the two steps. Shell and tube heat exchangers, for example, have been found to be useful, wherein the reaction mixture is preferably guided through the tubes and the cooling medium preferably through the shell of the heat exchanger.

The removal in step d) comprises at least three stages, wherein, in the first stage, a first membrane separation is effected, in which the rhodium catalyst system is enriched in the retentate and the permeate is directed to the next stage; In the membrane separation, the rhodium catalyst system is obtained in the retentate, while the aldehydes formed are enriched in the permeate. If high boilers are present, these are obtained at least partly in the permeate. The membrane separation itself can be effected at a temperature between 20 and 80° C., preferably 40 to 70° C. The transmembrane pressure in the membrane separation in step d) is preferably between 15 and 50 bar, preferably between 20 and 45 bar. In order to arrive at this transmembrane pressure, it may be necessary for an actuator to be present, which increases the pressure of the mixture guided to the membrane separation. One example is a pump or a pressure-increasing pump.

In the second stage of the removal in step d), a thermal separation is performed, in which at least a portion of the aldehydes formed is removed together with the top product, and the liquid bottom product is directed to the next stage.

The thermal separation in the second stage of the removal in step d) may be a distillation, a thin-film evaporation, a falling-film evaporation or a combination of two or more of these. However, the person skilled in the art may choose a suitable method in accordance with the demands of the respective process on the basis of their knowledge in the art. In a preferred embodiment of the present invention, the thermal separation is a thin-film evaporation, a falling-film evaporation or a combination of thin-film evaporation and falling-film evaporation. Thin-film evaporation and falling-film evaporation may also have a multistage configuration, i.e. take the form of what is caged a cascade. In a particularly preferred embodiment, the thermal separation is a multistage falling-film evaporation (evaporator cascade). If a thin-film evaporation, a falling-film evaporation or a combination of these is used for thermal separation, expansion after the first membrane separation step must be into a vacuum. i.e. a pressure of ≥10 mbar but less than 1 bar. Such an expansion is preferably effected in one step.

The membrane separation in the third stage of the removal in step d) may be effected in one or more stages, but is preferably effected in two or more stages. In the membrane separation, the rhodium catalyst system is obtained in the retentate, while the aldehydes formed are enriched in the permeate. If high boilers are present, these are at least partly obtained in the permeate, as a result of which they can be discharged from the process. This is because, in order to prevent enrichment of the high boilers in the process, a portion of the permeate or the entire permeate may be discharged from the process as purge. The rhodium catalyst system obtained in the retentate, by contrast, is preferably returned upstream of the first membrane separation in step d). The membrane separation itself can be effected at a temperature between 20 and 80° C., preferably 40 to 70° C. The transmembrane pressure in the membrane separation in step d) is preferably between 15 and 50 bar, preferably between 20 and 45 bar.

The aldehydes obtained from the process, as product of value, are usable in various ways in the chemical industry. For instance, these aldehydes may be used as a starting material. The aldehydes obtained are then sent to a downstream process step, for example a hydrogenation to give the alcohol or an oxidation to give the acid.

EXAMPLES

Example 1—Hydroformylation of Tri-n-Butene

In an industrial pilot plant comprising a reactor (cascaded bubble column), a thin-film evaporator and a membrane separation, hydroformylation experiments were conducted with tri-n-butene. For this purpose, a tri-n-butene stream was reacted with synthesis gas (50% CO/50% $H_2$) at about 270 bar and about 150° C. in the reactor. The biphasic product mixture containing the isotridecanal (ITDA) product, after optional cooling, is then expanded and separated in a thin-film evaporator (at <50 mbar), with removal of the product-containing phase. The residual stream is fed to a two-stage membrane separation (TMP 40 bar, temperature 50° C.), wherein the catalyst-containing retentate is guided to the reactor and the permeate is discharged as purge stream.

The experiment was conducted once with discharge cooling, i.e. cooling prior to the expansion, and once without discharge cooling. In each case, the rhodium use factor, i.e. the amount of rhodium in g required for production of one tonne of ITDA, was normalized to the value for the process conducted according to the prior art (=without cooling). The results can be seen in the table below.

|  | Rhodium use factor (normalized to prior art) |
|---|---|
| with prior cooling of the biphasic product mixture (inventive) | 0.67 |
| without prior cooling of the biphasic product mixture (prior art) | 1 |

It is clear from the table that the process can be conducted much more efficiently and less expensively since the use factor is distinctly smaller in the process with discharge cooling.

Example 2: Hydroformylation of Diisobutene

In a hydroformylation plant comprising, inter alia, a reactor (cascaded bubble column), a thin-film evaporator and a membrane separation, hydroformylation experiments were conducted with diisobutene. For this purpose, a diisobutene stream was reacted with synthesis gas (50% CO/50% $H_2$) at about 270 bar and about 130° C. in the presence of a rhodium catalyst system in the reactor. The biphasic product mixture that contains the TMH (trimethylhexanal) product, after optional cooling, is then expanded and separated in the thin-film evaporator (at <50 mbar), with removal of the product-containing phase. The residual stream is sent to a one-stage membrane separation (TMP 40 bar, temperature 50° C.), wherein the catalyst-containing retentate is guided to the reactor and the permeate is discharged as purge stream.

The experiment was conducted once with discharge cooling, i.e. cooling prior to the expansion, and once without discharge cooling. In each case, the rhodium use factor, i.e. the amount of rhodium in g required for production of one tonne of TMH, was normalized to the value for the process conducted according to the prior art (=without cooling). The results can be seen in the table below.

|  | Rhodium use factor (normalized to the prior art) |
|---|---|
| with prior cooling of the biphasic product mixture (inventive) | 0.685 |
| without prior cooling of the biphasic product mixture (prior art) | 1 |

It is clear from the table that the process can be conducted much more efficiently and less expensively since the use factor is distinctly smaller in the process with discharge cooling.

The invention claimed is:

1. A process for preparing aldehydes by hydroformylation of olefins, the process comprising:
    a) reacting $C_4$ to $C_{20}$ olefins in a hydroformylation in at least one reaction zone in the presence of a synthesis gas and a homogeneous rhodium catalyst system, at a pressure of 100 to 350 bar and a temperature of 90° C. to 250° C., to obtain a biphasic hydroformylation mixture comprising a gas phase and a liquid phase, wherein the biphasic hydroformylation mixture contains at least unconverted olefins, the synthesis gas, the homogeneous rhodium catalyst system, and aldehydes formed, which is withdrawn from the at least one reaction zone;
    b) expanding the biphasic hydroformylation mixture in a first expansion, to a pressure between 11 bar and 50 bar, and separating the biphasic hydroformylation mixture into a first gaseous phase comprising the synthesis gas, and a first liquid phase comprising the unconverted olefins, the homogeneous rhodium catalyst system, the aldehydes formed, and optionally, remaining synthesis gas;
    c) expanding the first liquid phase obtained from b) in a second expansion, to a pressure between 1 bar and 10 bar, and separating the first liquid phase into a second gaseous phase comprising the remaining synthesis gas, and a second liquid phase comprising the unconverted olefins, the homogeneous rhodium catalyst system, and the aldehydes formed; and d) feeding the second liquid phase to an at least three-stage removal, wherein, in the first stage, a first membrane separation is effected, in which the homogeneous rhodium catalyst system is enriched in a first retentate and a permeate is directed to the next stage;

in the second stage, the permeate from the first membrane separation is subjected to a thermal separation in which at least a portion of the aldehydes formed is removed together with a top product, and a liquid bottom product is directed to the third stage; and in the third stage, the liquid bottom product from the thermal separation is subjected to a second membrane separation in which the homogeneous rhodium catalyst system is enriched in a second retentate, wherein the biphasic hydroformylation mixture prior to the first expansion in b), the first liquid phase prior to the second expansion in c), or the second liquid phase prior to the feeding to the at least three-stage removal in d) is cooled to a temperature between 40 and 100° C.

2. The process according to claim 1, comprising both a first cooling of the biphasic hydroformylation mixture after the hydroformylation in a) and before the first expansion in b), and a second cooling of the second liquid phase after the second expansion in c) and before the at least three-stage removal in d).

3. The process according to claim 1, wherein the hydroformylation in a) Is effected at a pressure between 175 and 300 bar.

4. The process according to claim 1, wherein the hydroformylation in a) is effected at a temperature in a range from 120 to 200° C.

5. The process according to claim 1, wherein the $C_4$ to $C_{20}$ olefins used in the hydroformylation also function as solvent.

6. The process according to claim 1, wherein the homogeneous rhodium catalyst system used in the hydroformylation comprises rhodium and a phosphorus-containing ligand.

7. The process according to claim 1, wherein the first expansion in b) and/or the second expansion in c) is into a vessel in which gas phase and liquid phase can be separated.

8. The process according to claim 1, wherein the cooling is effected by a discharge cooler.

9. The process according to claim 1, wherein the first membrane separation and the second membrane separation in d) are effected at a temperature between 20 and 80° C.

10. The process according to claim 1, wherein a trans-membrane pressure in the first membrane separation and the second membrane separation in d) is between 15 and 50 bar.

11. The process according to claim 1, wherein the homogeneous rhodium catalyst system is obtained in the first retentate in the first membrane separation and the second retentate in the second membrane separation in d), and wherein the first retentate from the first membrane separation is returned to the at least one reaction zone in a), and the second retentate from the second membrane separation is recycled upstream of the first membrane separation in d).

12. The process according to claim 1, wherein the thermal separation is a distillation, a thin-film evaporation, a falling-film evaporation, or a combination of two or more thereof.

13. The process according to claim 12, wherein the thermal separation is the thin-film evaporation, the falling-film evaporation, or a combination of thin-film evaporation and falling-film evaporation.

14. The process according to claim 11, wherein the thermal separation is a multistage falling-film evaporation.

15. The process according to claim 1, wherein the aldehydes obtained from the process are sent to a downstream process.

16. The process according to claim 1, wherein the $C_4$ to $C_{20}$ olefins are $C_8$ to $C_{12}$ olefins.

17. The process according to claim 3, wherein the hydroformylation in a) is effected at a pressure between 200 and 280 bar.

18. The process according to claim 4, wherein the hydroformylation in a) is effected at a temperature in a range from 120 to 160° C.

19. The process according to claim 13, wherein the thermal separation is a multistage falling-film evaporation.

20. The process according to claim 15, wherein the downstream process is a hydrogenation or an oxidation.

* * * * *

UNITED STATES PATENT AND TRADEMARK OFFICE
CERTIFICATE OF CORRECTION

| | |
|---|---|
| PATENT NO. | : 11,773,041 B2 |
| APPLICATION NO. | : 18/055989 |
| DATED | : October 3, 2023 |
| INVENTOR(S) | : Frank Geilen et al. |

It is certified that error appears in the above-identified patent and that said Letters Patent is hereby corrected as shown below:

On the Title Page

Column 1, item (72) under INVENTORS, Line 4, currently reads, "Benedikt Dereks" and should read --Benedikt Dercks--; and Column 2, under OTHER PUBLICATIONS, Line 2, currently reads, "European Applicatiion" and should read --European Application--.

Signed and Sealed this
Ninth Day of January, 2024

Katherine Kelly Vidal
*Director of the United States Patent and Trademark Office*